United States Patent [19]

Riegel et al.

[11] Patent Number: 5,460,711
[45] Date of Patent: Oct. 24, 1995

[54] SENSOR FOR DETERMINING GAS CONSTITUENTS AND/OR GAS CONCENTRATIONS OF GAS MIXTURES

[75] Inventors: Johann Riegel, Bietigheim-Bissingen; Bernd Schumann, Rutesheim, both of Germany

[73] Assignee: Robert Bosch GmbH, Stuttgart, Germany

[21] Appl. No.: 169,351

[22] Filed: Dec. 20, 1993

[30] Foreign Application Priority Data

Dec. 23, 1992 [DE] Germany .......................... 42 43 733.4

[51] Int. Cl.[6] .................................................. G01N 27/41
[52] U.S. Cl. ........................ 204/425; 204/421; 204/424; 204/426; 204/429; 422/98
[58] Field of Search ....................... 204/153.18, 421–429; 422/98

[56] References Cited

U.S. PATENT DOCUMENTS

| | | | |
|---|---|---|---|
| 4,020,830 | 5/1977 | Johnson et al. | 204/426 |
| 4,158,166 | 6/1979 | Isenberg | 324/439 |
| 4,505,807 | 2/1985 | Yamada | 204/426 |
| 4,578,172 | 3/1986 | Yamada et al. | 204/426 |
| H427 | 2/1988 | Hirate et al. | 204/426 |
| 4,728,411 | 3/1988 | Mase et al. | 204/425 |
| 4,741,817 | 5/1988 | Croset et al. | 204/427 |
| 5,169,512 | 12/1992 | Wiedenmann et al. | 204/426 |
| 5,310,472 | 5/1994 | Dietz et al. | 204/426 |

*Primary Examiner*—T. Tung
*Attorney, Agent, or Firm*—Spencer, Frank & Schneider

[57] ABSTRACT

A sensor for determining at least one of gas constituents and gas concentrations in a gas mixture, such as CO, $NO_x$ and HC, in exhaust gas from an internal combustion engine, includes a semiconductor gas sensor having a gas sensitive region in communication with the gas mixture; a pumping cell including a solid electrolyte carrier and pumping electrodes disposed on the solid electrolyte carrier, the pumping cell being positioned in communication with the semiconductor gas sensor for effecting oxygen transfer to the semiconductor gas sensor on the side thereof opposite the gas mixture by pumping oxygen thereto to provide an $O_2$ mole current density in the gas sensitive region, and the pumping cell having a pumping current; a cover layer which is gas tight and which has a restricted opening defined therein provided on the pumping cell on the side thereof which communicates with the semiconductor gas sensor so that the oxygen is pumped through the restricted opening to the semiconductor gas sensor, whereby the $O_2$ mole current density in the gas sensitive region can be increased within the restricted opening while the pumping current remains constant, the gas sensitive region of the semiconductor gas sensor being disposed in the restricted opening so that an oxygen excess is established at the gas sensitive region due to the $O_2$ mole current density.

15 Claims, 1 Drawing Sheet

SENSOR FOR DETERMINING GAS CONSTITUENTS AND/OR GAS CONCENTRATIONS OF GAS MIXTURES

CROSS REFERENCE TO RELATED APPLICATION

This application claims the priority of Application Ser. No. P 42 43 733.4, filed Dec. 23rd, 1992, in the Federal Republic of Germany, the subject matter of which is incorporated herein by reference.

BACKGROUND OF THE INVENTION

The present invention is based on a sensor for the determination of gas constituents and/or gas concentrations in gas mixtures, particularly CO, $NO_x$ and HC in the exhaust gases of internal-combustion engines. Such a sensor includes a measuring element having a gas sensitive region as well as a pumping cell and pumping electrodes disposed on a solid electrolyte carrier for effecting oxygen transfer. The gas constituents to be determined will hereinafter be called contaminant constituents.

Probes of this type determine the contaminant concentration in exhaust gases by a change in the conductivity of, for example, semiconductive oxides or oxide mixtures. If conductivity is to be used for a measurement of The concentrations of oxidizable or reducible contaminants in exhaust gases, a transverse oxygen sensitivity results. If the oxygen partial pressures are particularly low and also in conjunction with high temperatures, metal oxides, for example $SnO_2$ or $In_2O_3$, experience a reduction of the metal oxide which results in malfunctioning of the sensor.

U.S. Pat. No. 4,158,166 discloses a method of measuring combustible constituents in a fuel-gas atmosphere wherein an electrochemical measuring cell and a pumping cell are provided. The measuring cell sets the electrical pumping potential to such a level that sufficient oxygen is pumped into the interior chamber to cause combustion of the combustible constituents. The amount of oxygen pumped is precisely the amount required to always produce a stoichiometric mixture at the measuring cell. The pumping current is utilized as a measure for the percentage of combustible constituents.

If oxygen is pumped toward the interior pumping electrode, the diffusion inhibiting effect of the protective layer causes an oxygen partial pressure which is higher than that of the exhaust gas to develop in the sensitive region. However, part of the oxygen diffuses through the layers and through the protective layer disposed between the sensitive region and the exhaust gas, and acting as a diffusion barrier, and reaches the oxygen-poor exhaust gas. The magnitude of the oxygen partial pressure is thus determined by the magnitude of the $O_2$ pumping current, the porosity of the individual layers, and the cross-sectional area determinative for the $O_2$ diffusion current. It is of advantage to have an excess oxygen or the highest possible oxygen partial pressure in the sensitive region compared to the oxygen partial pressure in the exhaust gas to thus eliminate as much as possible the dependency of the sensitive region on oxygen partial pressure fluctuations in the exhaust gas. This can be realized, on the one hand, by increasing the $O_2$ pumping current. However, any arbitrary increase of the pumping current is restricted to physical and electrochemical limits. On the other hand, the increase in oxygen partial pressure in the sensitive layer can be realized by a thicker and/or denser protective layer. However, this reduces the sensitivity of the sensitive region for the contaminant constituents to be measured in the exhaust gas.

ADVANTAGES AND SUMMARY OF THE INVENTION

The probe or sensor according to the invention, includes a measuring element which is arranged relative to the pumping cell such that the region of the pumping cell on the side of the gas mixture is covered by a gas-tight cover layer that is provided with a restricted opening toward the gas mixture so that the $O_2$ mole current density in the sensitive region of the measuring element can be increased. This has the advantage that an increase of the oxygen partial pressure in the sensitive region makes it possible to increase the $O_2$ mole current density without it being necessary to increase the $O_2$ pumping current. Thus it is possible at the same time to substantially eliminate the $O_2$ transverse sensitivity of the sensor. To manufacture the sensor according to the present invention it is merely necessary to provide an additional screen-printing step for applying the cover layer.

The measures defined in the dependent claims provide for advantageous modifications and improvements of the sensor defined in the main claim. A particularly simple embodiment is obtained by a combination of the electrochemical pumping cell with a resistance measuring sensor, with a gas-tight cover layer enclosing a volume in which the internal pumping electrode is disposed. The sensitive region is disposed in a recess in the cover layer in which the oxygen mole current density is higher.

BRIEF DESCRIPTION OF THE DRAWINGS

Two embodiments of the invention are illustrated in the drawing figures and will be described in greater detail below.

DETAILED DESCRIPTION OF THE PREFERRED EMBODIMENTS

Figure 1:
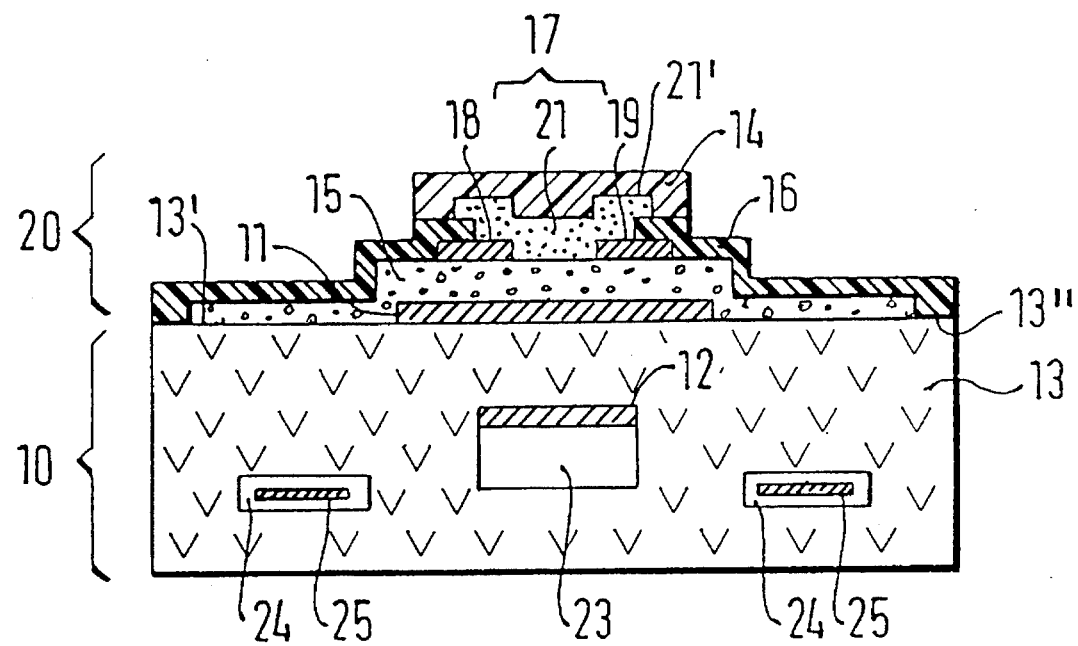
FIG. 1 is a sectional view of a first embodiment of a sensor according to the invention.

The sensor according to FIG. 1 is composed of an electrochemical pumping cell 10 and a measuring element 20. Pumping cell 10 includes a solid electrolyte carrier 13 of an $O_2$ ion conducting solid electrolyte composed, for example, of stabilized zirconium oxide. A gas channel 23 and a heating conductor 25 embedded in a heater insulation 24 are disposed within solid electrolyte carrier 13. An internal pumping electrode 11 is applied to the large surface 13' of the solid electrolyte carrier 13. Opposite it, an external pumping electrode 12 is arranged in the gas channel 23. Gas channel 23 is in communication either with the measuring gas or with an $O_2$ atmosphere. The configuration of such a pumping cell and its manufacture have already been disclosed in German Patent No. 3,811,713 (corresponding to U.S. Pat. No. 5,169,512). Gas channel 23 may also be omitted in which case electrode 12 is exposed directly to the measuring gas.

Measuring element 20 is a resistance measuring sensor including a first measuring electrode 18 and a second measuring electrode 19, as well as a gas sensitive, semiconductive metal oxide layer 21. To form the complete sensor, a porous insulating layer 15, for example of $Al_2O_3$, is placed over the internal pumping electrode 11. The porous insulating layer 15 then extends over the surface 13' of the solid electrolyte carrier 13 except for an edge region 13" remaining on both sides. The two spaced measuring electrodes 18 and 19, composed, for example, of a platinum cermet compound, are disposed on the porous insulation layer 15.

A gas-tight cover layer 16 is disposed above the insulation layer 15. In the present embodiment, the layer 16 extends to solid electrolyte carrier 13 in the surface portions 13" so that the porous insulating layer 15 is closed toward the solid electrolyte carrier 13. In the present embodiment, cover layer 16 extends over approximately half of each of the measuring electrodes 18 and 19 so that a restricted opening 17 results above (and between) measuring electrodes 18 and 19. Metal oxide layer 21, which is composed, for example, of $SnO_2$, is disposed within the restricted opening 17. In the present embodiment, metal oxide layer 21 laterally extends beyond the restricted opening 17 so that metal oxide layer 21 forms an edge 21' on the surface of the cover layer 16. The resistance measuring sensor is also manufactured by screen-printing, with the application of the individual layers being effected analogously to the method disclosed in German Patent 2,908,916.

Figure 2:
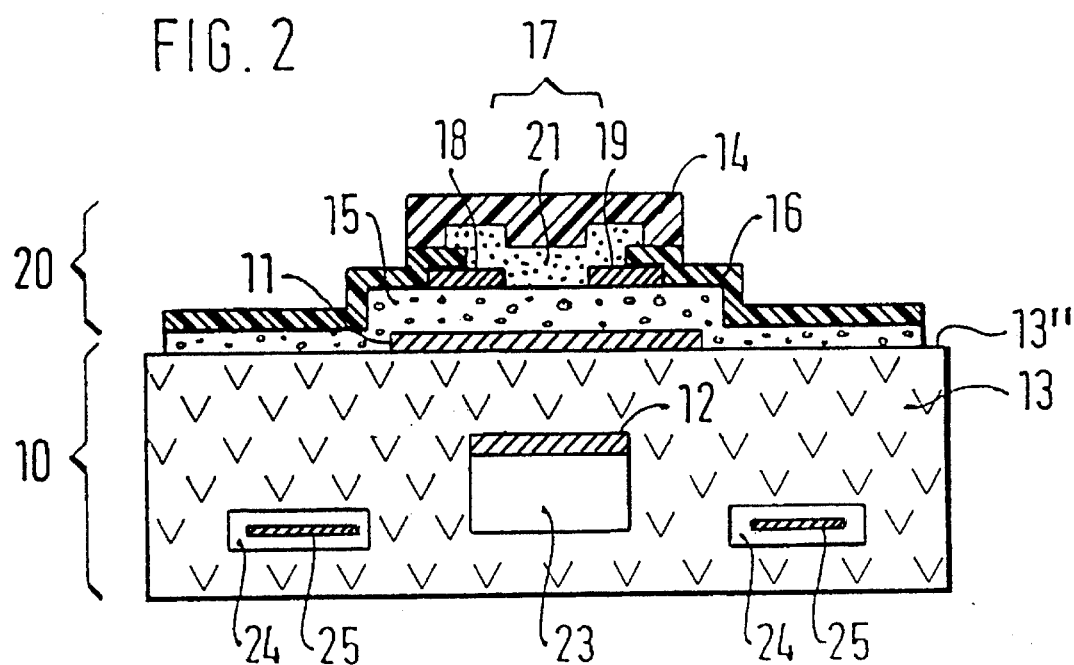
FIG. 2 is a sectional view of a second embodiment of a sensor according to the invention.

FIG. 2 depicts a second embodiment in which the sensor has essentially the same configuration as in the first embodiment. The only difference from the embodiment according to FIG. 1 is that the porous insulation layer 15 is laterally exposed and is not enclosed by cover layer 16. i.e., the sensor layer 16 does not extend to the surface portions 13". With this arrangement, an electrically conductive layer can be employed as the gas-tight cover layer 16 without creating transverse conductivity through pumping cell 10.

The arrangement of cover layer 16 and the formation of the restricted opening 17 reduce the cross-section of the sensitive region that is exposed to the measuring gas. Thus the $O_2$ mole current density in the sensitive region of measuring element 20 is increased while the pumping current remains the same.

In addition, toward the measuring gas, the sensor is provided with a porous protective layer 14 which constitutes a diffusion barrier. In the present embodiments, protective layer 14 is disposed above metal oxide layer 21, with it also being possible for protective layer 14 to extend over the entire width of the sensor or to encase the sensor as a whole. It is also conceivable to pull the protective layer 14 of the second embodiment down to the surface portion 13" of solid electrolyte carrier 13 so that the porous insulating layer 15 is encased.

In addition, an embodiment is conceivable in which the measuring electrodes 18 and 19 are disposed on cover layer 16. This embodiment has the advantage that the size of the restricted opening 17 can be reduced to the point where the spacing between electrodes 18 and 19 reaches the minimum size that can be manufactured by a printing press and thus permit the realization of a maximum possible increase in the $O_2$ mole current density.

The gas-tight cover layer 16 may be composed, for example, of $ZrO_2$ or $Al_2O_3$. Thanks to cover layer 16, a greater oxygen partial pressure can be set in the sensitive region of measuring element 20. In addition, it is thus also possible to realize an equally high oxygen partial pressure with a thinner and less dense protective layer (diffusion barrier), thus obtaining greater sensitivity of the sensitive region of measuring element 20 for the gas constituents (CO, $NO_x$, HC) to be measured in the exhaust gas.

It will be understood that the above description of the present invention is susceptible to various modifications, changes and adaptations, and the same are intended to be comprehended within the meaning and range of equivalents of the appended claims.

What is claimed is:

1. A sensor for determining at least one of gas constituents and gas concentrations in a gas mixture, comprising:

a semiconductor gas sensor having a gas sensitive region in communication with the gas mixture;

a pumping cell comprised of a solid electrolyte carrier and pumping electrodes disposed on the solid electrolyte carrier, the pumping cell being positioned in communication with the semiconductor gas sensor for effecting oxygen transfer to the semiconductor gas sensor on the side thereof opposite the gas mixture by pumping oxygen thereto to provide an $O_2$ mole current density in the gas sensitive region, and the pumping cell having a pumping current;

a cover layer which is gas tight and which has a restricted opening defined therein provided on the pumping cell on the side thereof which communicates with the semiconductor gas sensor so that the oxygen is pumped through the restricted opening to the semiconductor gas sensor, whereby the $O_2$ mole current density in the gas sensitive region can be increased within the restricted opening while the pumping current remains constant, the gas sensitive region of the semiconductor gas sensor being disposed within the restricted opening so that an oxygen excess is established at the gas sensitive region due to the $O_2$ mole current density.

2. The sensor as defined in claim 1, wherein the pumping electrodes include an internal pumping electrode which is disposed on the surface of the solid electrolyte carrier which is closest to the semiconductor gas sensor, and wherein the cover layer encloses a volume within which the internal pumping electrode is accommodated.

3. The sensor as defined in claim 2, wherein a porous insulating layer which is comprised of an insulating porous material is applied to the internal pumping electrode and to at least a part of the surface of the solid electrolyte carrier which is closest to the semiconductor gas sensor, and wherein the cover layer is placed over the porous insulating layer.

4. The sensor as defined in claim 3, wherein the cover layer extends to the surface of the solid electrolyte carrier so that the porous insulating layer is enclosed by the cover layer.

5. The sensor as defined in claim 4, wherein at least the semiconductor gas sensor is covered by a porous protective layer comprised of a porous material.

6. The sensor as defined in claim 3, wherein the porous insulating layer has lateral extremities which are open to ambient so as to provided a lateral diffusion opening for the gas mixture to diffuse therethrough.

7. The sensor as defined in claim 6, wherein at least the semiconductor gas sensor is covered by a porous protective layer comprised of a porous material.

8. The sensor as defined in claim 3, wherein at least the semiconductor gas sensor is covered by a porous protective layer comprised of a porous material.

9. The sensor as defined in claim 1, wherein at least the semiconductor gas sensor is covered by a porous protective layer comprised of a porous material.

10. The sensor as defined in claim 9, wherein the semiconductor gas sensor is comprised of a metal oxide layer and a pair of spaced measuring electrodes which are disposed between the metal oxide layer and a porous insulating layer.

11. The sensor as defined in claim 10, wherein the metal oxide layer has a edge, and wherein the edge of the metal oxide layer extends over the cover layer which is gas tight.

12. The sensor as defined in claim 1, wherein the semiconductor gas sensor is comprised of a metal oxide layer and a pair of spaced measuring electrodes which are disposed between the metal oxide layer and a porous insulating layer, wherein the pumping electrodes include an internal pumping electrode which is disposed on the surface of the solid electrolyte carrier which is closest to the semiconductor gas sensor, wherein the porous insulating layer is applied to the internal pumping electrode and to the surface of the solid electrolyte carrier which is closest to the semiconductor gas sensor;

wherein the semiconductor gas sensor is disposed on the porous insulating layer with the metal oxide layer thereof being disposed on the porous insulating layer between the pair of spaced measuring electrodes and extending laterally over a portion of the pair of spaced measuring electrodes, and wherein the cover layer covers the porous insulating layer and a remaining portion of the pair of spaced measuring electrodes.

13. The sensor as defined in claim 12, wherein the metal oxide layer has an edge, and wherein the edge of the metal oxide layer extends over the cover layer which is gas tight.

14. The sensor as defined in claim 13, wherein at least the metal oxide layer is covered by a protective layer which is porous.

15. The sensor as defined in claim 1, wherein the gas mixture comprises gas constituents including at least one of CO, $NO_x$ and HC, and wherein the gas mixture is exhaust gas from an internal combustion engine.

* * * * *